United States Patent [19]

Schmitt

[11] Patent Number: 4,555,367

[45] Date of Patent: Nov. 26, 1985

[54] PURIFICATION OF ACRYLONITRILE

[75] Inventor: Joseph M. Schmitt, Ridgefield, Conn.

[73] Assignee: American Cyanamid Company, Stamford, Conn.

[21] Appl. No.: 571,631

[22] Filed: Jan. 3, 1984

Related U.S. Application Data

[63] Continuation of Ser. No. 362,364, Mar. 26, 1982, abandoned, Continuation-in-part of Ser. No. 258,104, Apr. 27, 1981, abandoned.

[51] Int. Cl.$^4$ ............................................. C07C 121/32
[52] U.S. Cl. .................................................... 260/465.9
[58] Field of Search ...................................... 260/465.9

[56] References Cited

U.S. PATENT DOCUMENTS

| | | | |
|---|---|---|---|
| 2,444,589 | 7/1948 | Blann | 260/465.9 X |
| 2,622,097 | 12/1952 | Osborne | 260/465.9 |
| 2,812,312 | 11/1957 | Wilkinson | 260/465.9 X |
| 2,963,459 | 12/1960 | Nicholson et al. | 260/83.5 |
| 3,017,426 | 1/1962 | Ruffing et al. | 260/465.9 |
| 3,133,121 | 5/1964 | Ager, Jr. et al. | 260/465.9 |
| 3,146,258 | 8/1964 | Leach | 260/465.9 |
| 3,201,450 | 8/1965 | Cohen et al. | 260/465.9 X |
| 3,203,977 | 8/1965 | Fein et al. | 260/465.9 X |
| 3,238,152 | 3/1966 | Horn | 260/465.9 X |
| 3,265,726 | 8/1966 | Green et al. | 260/465.9 |

OTHER PUBLICATIONS

Stone, et al., J. Chem. Soc., (1950), pp. 2755–2759.

*Primary Examiner*—Joseph Paul Brust
*Attorney, Agent, or Firm*—John W. Cornell

[57] ABSTRACT

Acrylonitrile which contains small amounts of acrolein or other aldehydes may be purified by contacting the acrylonitrile with a compound containing at least one —B—H moiety.

8 Claims, No Drawings

PURIFICATION OF ACRYLONITRILE

CROSS REFERENCE TO RELATED APPLICATION

This application is a continuation of application Ser. No. 362,364, filed Mar. 26, 1982, now abandoned, which is in turn a continuation-in-part of application Ser. No. 258,104 filed Apr. 27, 1981, now abandoned.

This application relates to a composition comprising acrylonitrile and a borane compound and to a process for purification of acrylonitrile containing aldehyde impurities. More particularly, this invention relates to such a composition and process wherein derivatives prepared from the purified acrylonitrile provide improved polymers.

Acrylonitrile as conventionally prepared has been found to contain small amounts (parts per million) of aldehyde impurities. A critical impurity has been found to be acrolein. When acrylamide is made from such acrolein-contaminated acrylonitrile and the acrylamide is polymerized for use as flocculants, the resultant polyacrylamide is oftentimes unsatisfactory in that it contains large amounts of insoluble material and/or is not of a sufficient molecular weight for commercial use.

Japanese Application No. 53-60040 (Publication No. 54-151915 of Mitsui Toatsu) discloses the use of a porous-form ion exchange resin which possesses a primary and/or secondary amine to perform the removal of acrolein.

However, this procedure has not been found to be entirely satisfactory and research continues towards finding other methods for dealing with the problem.

In accordance with the present invention, there is provided a composition comprising acrylonitrile and a borane compound containing at least one —B—H moiety selected from borohydrides and complexes of boron hydrides.

There is also a process for purifying acrylonitrile which comprises contacting an impure acrylonitrile with an effective amount of a borane compound containing at least one —B—H moiety selected from borohydrides and complexes of boron hydrides.

In accordance with the present invention, the acrolein content in conventionally prepared acrylonitrile may be greatly reduced by contacting said acrylonitrile with an effective amount of a borane compound for a sufficient time to reduce the acrolein content. Compounds containing at least one —B—H moiety are referred to herein as boranes. Generally, these compounds have been reported to be catalysts for the polymerization of acrylonitrile and other monomers in the absence of oxygen, c.f. U.S. Pat. No. 2,963,459. However, as shown in Example 3 below, when sodium borohydride was mixed into acrylonitrile per se under a nitrogen atmosphere, no polymerization of the acrylonitrile occurred.

The boranes useful herein include borohydrides, complexes of boron hydrides with other compounds and resins which contain a —B—H moiety.

Examples of borohydrides useful herein include but are not limited to the boronhydrides (tetrahydroborates) of sodium, potassium, rubidium, cesium, calcium, barium, strontium, magnesium, thorium, mercury, gold and lead; the cyanoborohydrides of the above metals; Lalancette's Reagent ($NaBH_2S_3$); hydroidotrialkoxyborates of the above metals; tetramethyl ammonium octahydrotriborate as well as other hydropolyborates, e.g. salts of $B_{12}H_{12}^{-2}$; and the like.

Examples of complexes of boron hydrides with other compounds include the amine boranes wherein amines are combined with tetrahydroborates. Suitable such amines include ammonia, methylamine, dimethylamine, trimethylamine, triethylamine, isopropylamine, t-butylamine, N,N-dimethyl-2-methoxyethylamine, pyridine, piperazine, morpholine, methylmorpholine, 2,6-lutidine, methoxypyridine, 4-aminopyridine and the like.

Examples of resins useful herein include the Amborane ® resins of Rohm and Haas, as well as such as poly(4-vinylpyridine)-borane. These amine-boranes have polymeric backbones.

Any borane compound to be useful herein must, of course, have sufficient stability in the monomer composition to provide the desired benefits described.

When the borane compound is used in the form of a borohydride or a boron hydride complex, and not as a resin, it should be used in an amount and for a time sufficient to reduce the acrolein content to the extent desired. Generally, an amount in the range of from about 50 parts per million up to about 2 weight percent based on the weight of the acrylonitrile will be suitable. Preferably, about 100 to 5000 parts per million are used. Correspondingly, the treatment time may range from as little as 5 minutes up to 7 days or longer. Preferably the time is for about 10 minutes to about 3 hours.

When the borane is used as a resin, conventional techniques may be used to induce good contact between the liquid acrylonitrile and the resin while the length of any column and the treatment time may be adjusted as necessary.

In the following non-limiting examples all parts and percentages are by weight unless otherwise specified.

EXAMPLE 1

To a 4-ounce screw cap bottle are added 50 grams (g) of acrylonitrile (AN) and a magnetic stirrer. Thereafter sodium borohydride is added in the form and the amounts shown in the Table below. The acrolein content is measured at the beginning of the test and at the times indicated in the Table.

The results clearly demonstrate that the sodium borohydride treatment reduces the acrolein content. No polymerization of the acrylonitrile is observed.

TABLE

Results of Example 1

| $NaBH_4$ ppm/AN | Added as | Reaction Time | Acrolein Before | Acrolein After |
| --- | --- | --- | --- | --- |
| 50 | 2.5% aqueous | 4 days | 5.2 | 3.4 |
| 50 | 2.5% aqueous | 3.5 days | 24.0 | 6.0 |
| 500 | 2.5% aqueous | 2 days | 24.0 | 1.5 |
| 500 | powder | 4 days | 24.0 | 1.7 |
| 500 | 2.5% aqueous | 10 minutes | 24.0 | 1.2 |
|  |  | 1 hour |  | 0.6 |
|  |  | 3 hours |  | 1.4 |
|  |  | 19 hours |  | 1.4 |
|  |  | 2 days |  | 0.2 |
| 500 | powder | 10 minutes | 24.0 | 1.8 |
|  |  | 1 hour |  | 1.2 |
|  |  | 3 hours |  | 2.7 |
|  |  | 19 hours |  | 5.2 |
|  |  | 2 days |  | 1.5 |

EXAMPLE 2

Two columns are filled with Amborane ® 345 and 355 respectively and acrylonitrile containing 1.3 parts per million acrolein is passed through each column under flood conditions. The acrolein content of the exiting acrylonitrile is measured to determine the effectiveness of the treatment. The results are as follows:

| Resin | Acrolein Content | |
|---|---|---|
| | After 1 Bed Volume AN | After 10 Bed Volumes AN |
| Amborane 345 | .1 | .5 |
| Amborane 355 | .1 | 1.2 |

The resins remove the acrolein but the treatment capacity of the resin is limited.

EXAMPLE 3

(a) Acrylonitrile in the amount of 125 g and containing about 4 ppm acrolein is placed in a reaction vessel and purged with nitrogen for 20 minutes. Then sodium borohydride powder is added in the amount of 500 ppm (0.0625 g) based on the acrylonitrile with the nitrogen purge continuing throughout.

After 15.5 hours no polymerization of the acrylonitrile is observed and the acrolein content is less than 2 ppm.

(b) The procedure of (a) above is repeated except that the borohydride is added in the amount of 2000 ppm (0.25 g). Again, no polymerization of the acrylonitrile occurred and the acrolein content is similarly reduced.

What is claimed is:

1. A method for reducing the acrolein impurity content in an acrylonitrile monomer composition containing a finite amount of acrolein impurity in an amount of 24 parts per million or less of acrolein, said method comprising contacting the acrylonitrile-acrolein mixture with an amount of an alkali metal borohydride effective to reduce the content of said acrolein impurity but insufficient to catalyze polymerization of said acrylonitrile monomer composition.

2. An improved acrylonitrile monomer composition obtained by:
    contacting an acrylonitrile monomer composition comprising acrylonitrile and an amount of about 24 parts per million, or less, based on the weight of acrylonitrile, of an aldehyde impurity comprising acrolein with an amount of an alkali metal borohydride effective to reduce the content of said aldehyde impurity but insufficient to catalyze polymerization of said acrylonitrile monomer composition.

3. The composition of claim 2 wherein said alkali metal borohydride is sodium borohydride.

4. The composition of claim 2 wherein said alkali metal borohydride is added in an amount of from about 50 parts per million to about 2 weight percent based on the weight of said acrylonitrile.

5. The composition of claim 2 wherein said alkali metal borohydride is added in an amount of about 100 to 5,000 parts per million based on the weight of said acrylonitrile.

6. The method of claim 1 wherein said alkali metal borohydride is sodium borohydride.

7. The method of claim 1 wherein said alkali metal borohydride is contacted with said acrylonitrile in an amount of about 50 parts per million to about 2 weight percent based on the weight of said acrylonitrile and for a time of from about 5 minutes to 7 days.

8. A process according to claim 1 wherein said alkali metal borohydride is contacted with said acrylonitrile in an amount of about 100 to 5,000 parts per million based on the weight of said acrylonitrile and for a time of from about 10 minutes to 3 hours.

* * * * *